(12) United States Patent
Srimohanarajah et al.

(10) Patent No.: US 10,603,118 B2
(45) Date of Patent: Mar. 31, 2020

(54) METHOD FOR RECOVERING PATIENT REGISTRATION

(71) Applicants: Kirusha Srimohanarajah, Toronto (CA); Gal Sela, Toronto (CA); Dorothy Lui, Toronto (CA); Kai Michael Hynna, Toronto (CA)

(72) Inventors: Kirusha Srimohanarajah, Toronto (CA); Gal Sela, Toronto (CA); Dorothy Lui, Toronto (CA); Kai Michael Hynna, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 335 days.

(21) Appl. No.: 15/796,002

(22) Filed: Oct. 27, 2017

(65) Prior Publication Data

US 2019/0125451 A1    May 2, 2019

(51) Int. Cl.
| | |
|---|---|
| *G06K 9/00* | (2006.01) |
| *A61B 34/20* | (2016.01) |
| *G06Q 50/24* | (2012.01) |
| *G16H 10/60* | (2018.01) |
| *G16H 30/40* | (2018.01) |

(Continued)

(52) U.S. Cl.
CPC ............ *A61B 34/20* (2016.02); *G06Q 50/24* (2013.01); *G16H 10/60* (2018.01); *G16H 20/40* (2018.01); *G16H 30/40* (2018.01); *A61B 17/34* (2013.01); *A61B 34/10* (2016.02); *A61B 90/36* (2016.02); *A61B 2034/107* (2016.02); *A61B 2034/2055* (2016.02); *A61B 2090/363* (2016.02); *A61B 2090/374* (2016.02); *A61B 2090/3735* (2016.02)

(58) Field of Classification Search
None
See application file for complete search history.

(56) References Cited

U.S. PATENT DOCUMENTS

| | | |
|---|---|---|
| 6,560,354 B1 | 5/2003 | Maurer, Jr. et al. |
| 2005/0148859 A1 | 7/2005 | Miga et al. |

(Continued)

FOREIGN PATENT DOCUMENTS

| | | |
|---|---|---|
| GB | 2567721 A | 4/2019 |
| WO | 2010/036444 A1 | 4/2010 |

OTHER PUBLICATIONS

Search report issued by the Intellectual Property Office of the United Kingdom in relation to corresponding GB Application No. GB1817324.5 dated Apr. 30, 2019, 5 pgs.

*Primary Examiner* — Atiba O Fitzpatrick
(74) *Attorney, Agent, or Firm* — Rowand LLP (57) ABSTRACT

A method for updating a patient registration during a surgical procedure is disclosed. The surgical procedure uses an optical navigation system for optically tracking a patient reference object in a real world space and includes intraoperatively acquiring a first set of image data depicting a region of interest on the patient while the first registration is intact. The region of interest includes at least one anatomical landmark. The method includes: detecting that the first registration has been lost; obtaining a second set of image data depicting the region of interest; identifying a transform based on the first set of image data and the second set of image data; and applying the identified transform to data points of the first registration to obtain data points for the updated patient registration.

18 Claims, 9 Drawing Sheets

(51) Int. Cl.
*G16H 20/40* (2018.01)
*A61B 90/00* (2016.01)
*A61B 34/10* (2016.01)
*A61B 17/34* (2006.01)

(56) References Cited

U.S. PATENT DOCUMENTS

| | | |
|---|---|---|
| 2008/0119725 A1 | 5/2008 | Lloyd |
| 2015/0320512 A1 | 11/2015 | Gassner et al. |
| 2016/0000515 A1* | 1/2016 | Sela ................. G06T 7/337 600/424 |
| 2018/0168735 A1* | 6/2018 | Lui .................... G06T 7/33 |
| 2018/0200002 A1* | 7/2018 | Kostrzewski ......... G02C 7/049 |
| 2018/0235714 A1* | 8/2018 | Kuo ..................... A61B 34/20 |
| 2018/0333141 A1* | 11/2018 | Pardasani ............ A61B 8/0808 |
| 2019/0060004 A1* | 2/2019 | Witcomb ............... G06T 7/30 |

* cited by examiner

METHOD FOR RECOVERING PATIENT REGISTRATION

FIELD

The present disclosure relates to a system and method for recovering patient registration during image-guided surgical procedures.

BACKGROUND

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimens, and radiation therapy are only a few examples of procedures utilizing imaging guidance in the medical field.

Advanced imaging modalities such as Magnetic Resonance Imaging (MRI) have led to improved rates and accuracy of detection, diagnosis and staging in several fields of medicine including neurology, where imaging of diseases such as brain cancer, stroke, Intra-Cerebral Hemorrhage (ICH), and neurodegenerative diseases, such as Parkinson's and Alzheimer's, are performed. As an imaging modality, MRI enables three-dimensional visualization of tissue with high contrast in soft tissue without the use of ionizing radiation. This modality is often used in conjunction with other modalities such as Ultrasound (US), Positron Emission Tomography (PET) and Computed X-ray Tomography (CT), by examining the same tissue using the different physical principals available with each modality. CT is often used to visualize boney structures and blood vessels when used in conjunction with an intra-venous agent such as an iodinated contrast agent. MRI may also be performed using a similar contrast agent, such as an intra-venous gadolinium based contrast agent which has pharmaco-kinetic properties that enable visualization of tumors and break-down of the blood brain barrier. These multi-modality solutions can provide varying degrees of contrast between different tissue types, tissue function, and disease states. Imaging modalities can be used in isolation, or in combination to better differentiate and diagnose disease.

In neurosurgery, for example, brain tumors are typically excised through an open craniotomy approach guided by imaging. The data collected in these solutions typically consists of CT scans with an associated contrast agent, such as iodinated contrast agent, as well as MRI scans with an associated contrast agent, such as gadolinium contrast agent. Optical imaging is often used in the form of a microscope to differentiate the boundaries of the tumor from healthy tissue, known as the peripheral zone. Tracking of instruments relative to the patient and the associated imaging data is also often achieved by way of external hardware systems such as mechanical arms, or radiofrequency or optical tracking devices. As a set, these devices are commonly referred to as surgical navigation systems.

During a medical procedure, navigation systems require a registration process to transform between the physical position of the patient in the operating room and the volumetric image set (e.g., MRI/CT) being used as a reference to assist in accessing the target area in the patient. Conventionally, this registration is done relative to the position of a patient reference, which is visible by the tracking system and stays fixed in position and orientation relative to the patient throughout the procedure.

This registration is typically accomplished through a touch-point registration method which involves constructing a correspondence of identifiable points (e.g., either fiducial or anatomic points) between the patient in the operating room and the volumetric image set of the patient. Such an approach to registration has a number of disadvantages, such as those that increase effort on the parts of the surgical team including requiring fiducials to be placed before patient scans, requiring points to be identified one at a time, requiring points to be reacquired. Additionally, disadvantages of this method also affect the accuracy of the guidance system, such as providing for a limited number of points, touch point collection is subject to user variability, and the physical stylus used for collecting the points can deform or deflect patient skin position, in addition the patient is required to be imaged directly before the procedure and the fiducials may move/fall off.

Another approach to performing a registration is the surface trace registration method which involves acquiring a contour of the patient, by drawing a line over the surface of the patient, usually acquiring a series of points, using either a tracked stylus pointer or a laser pointer and fitting that contour to the corresponding extracted surface from an image of the patient.

The patient reference (e.g. a tracked reference marker) is placed in a fixed position relative to the patient anatomy of interest. Generally, this can be accomplished by securing the patient reference to a patient immobilization frame, such as a neurosurgical head holder (skull clamp) system like the MAYFIELD® skull clamp, which is itself rigidly attached to the patient. In the course of a surgical procedure, the patient reference and/or parts of the patient's body may be inadvertently bumped or moved, resulting in a loss of registration. Inaccuracies in image guidance can have serious adverse consequences on the outcome of the clinical procedure. As such, after the detection of a loss of registration, the patient anatomy may need to be re-registered or, in some cases, navigation may be disabled for the remainder of the surgical procedure.

SUMMARY

In an aspect, the present disclosure provides a computer-implemented method for updating a patient registration during a surgical procedure that uses an optical navigation system for optically tracking a patient reference object in a real world space. The surgical procedures includes intraoperatively acquiring a first set of image data depicting a region of interest on the patient while the first registration is intact, where the region of interest includes at least one anatomical landmark. The method for updating the patient registration includes: detecting that the first registration has been lost; obtaining a second set of image data depicting the region of interest; identifying a transform based on the first set of image data and the second set of image data; and applying the identified transform to data points of the first registration to obtain data points for the updated patient registration.

In another aspect, the present disclosure provides a computer-implemented method for updating a first patient registration during a surgical procedure that uses an optical navigation system for optically tracking a patient reference object in a real world space. The surgical procedure includes intra-operatively acquiring first image data while the first registration is intact, where the first image data depicts the patient reference object and a region of interest on the patient that includes at least one anatomical landmark. The method for updating the first patient registration includes: detecting that the first registration has been lost; obtaining second image data depicting the patient reference object and the region of interest; identifying a transform based on the first image data and the second image data; and applying the identified transform to data points of the first patient registration to obtain data points for the updated patient registration.

BRIEF DESCRIPTION OF DRAWINGS

Reference will now be made, by way of example, to the accompanying drawings which show example embodiments of the present application and in which.

DETAILED DESCRIPTION OF EXAMPLE EMBODIMENTS

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein, the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

The present disclosure describes methods for recovering from a loss of patient registration. In surgical procedures, such as a craniotomy, where identifiable features are created on the patient anatomy as a part of the procedure (e.g. a craniotomy opening), intraoperatively acquired image and scan data can be used to identify the relative change in position of a part of the patient's body with respect to the patient reference. A spatial transform can be derived from the identified change in position, and said transform may be used to obtain an updated (corrected) patient registration. This technique of using data (i.e. intraoperatively acquired images and scans) that is already available as a component of the clinical workflow obviates the need to take additional action to effect recovery of a registration. In particular, the approach presented in the present disclosure does not require the active setting of recovery points (e.g. drilling of recovery points on a patient's skull) prior to the surgical procedure, which is an added step that may suffer from inconsistency and variability depending on the surgeon performing the procedure.

In the example of a port-based surgery, a surgeon or robotic surgical system may perform a surgical procedure involving tumor resection in which the residual tumor remaining after is minimized, while also minimizing the trauma to the healthy white and grey matter of the brain. In such procedures, trauma may occur, for example, due to contact with the access port, stress to the brain matter, unintentional impact with surgical devices, and/or accidental resection of healthy tissue. A key to minimizing trauma is ensuring that the spatial location of the patient as understood by the surgeon and the surgical system is as accurate as possible.

The phrase "registration" or "image registration" refers to the process of determining the transform to be used in correlating three-dimensional points across different coordinate systems. Registration links two different coordinate systems so that data positioned in one coordinate system may be mapped to the other coordinate system using the transform. Data may include photographs, data from different sensors, times, depths, or viewpoints. The process of "registration" is used in some of the described examples for medical imaging in which images from different imaging modalities are co-registered. Registration is used in order to be able to compare or integrate the data obtained from these different modalities for presentation on a common platform or display.

When it comes to registration of imaging data with optical tracking data, those skilled in the relevant arts will appreciate that there are numerous registration techniques available and one or more of the techniques may be applied in implementations of the present application. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Figure 1:
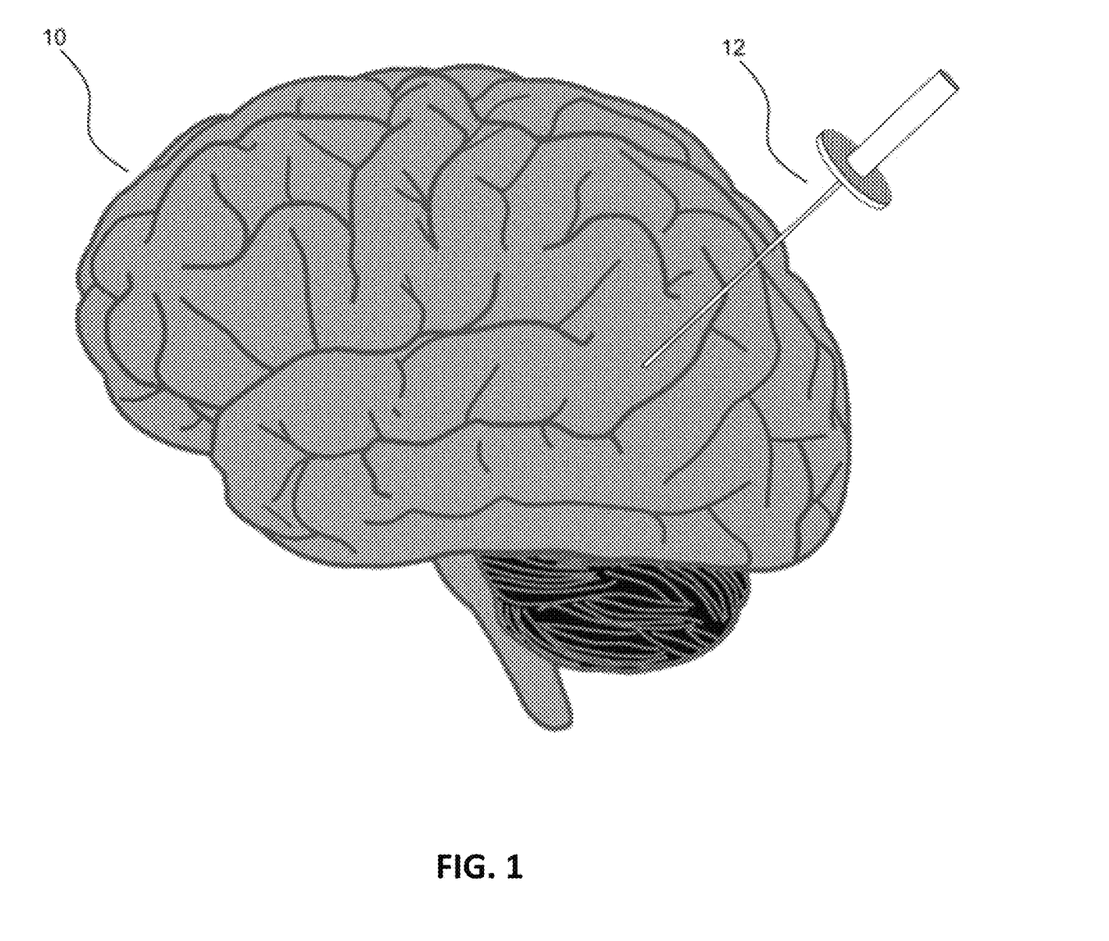
FIG. 1 illustrates the insertion of an access port into a human brain, for providing access to internal brain tissue during a medical procedure.

FIG. 1 illustrates the insertion of an access port into a human brain, for providing access to internal brain tissue during a medical procedure. In FIG. 1, access port 12 is inserted into a human brain 10, providing access to internal brain tissue. Access port 12 may include instruments such as catheters, surgical probes, or cylindrical ports. Surgical tools and instruments may then be inserted within the lumen of the access port in order to perform surgical, diagnostic or therapeutic procedures, such as resecting tumors as necessary. The present disclosure applies equally well to catheters, deep brain stimulation (DBS) needles, a biopsy procedure, and also to biopsies and/or catheters in other medical procedures performed on other parts of the body where head immobilization is needed.

In the example of a port-based surgery, a straight or linear access port 12 is typically guided down a sulci path of the brain. Surgical instruments would then be inserted down the access port 12.

Optical tracking systems, which may be used in the medical procedure, track the position of a part of the instrument that is within line-of-site of the optical tracking camera. In some embodiments these optical tracking systems also require a reference to the patient to know where the instrument is relative to the target (e.g., a tumor) of the medical procedure. These optical tracking systems require a knowledge of the dimensions of the instrument being tracked so that, for example, the optical tracking system knows the position in space of a tip of a medical instrument relative to the tracking markers being tracked.

Figure 2:
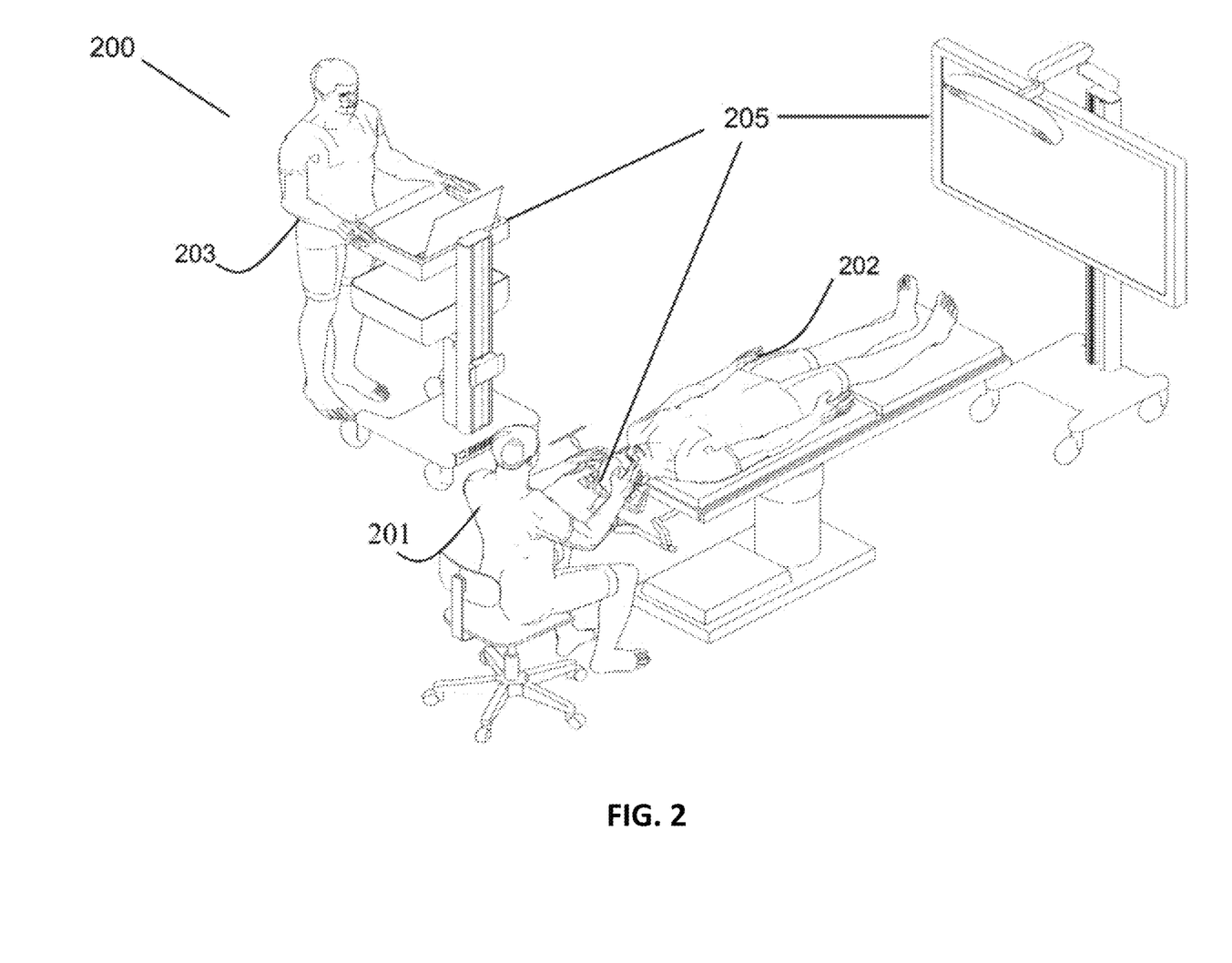
FIG. 2 shows an exemplary navigation system to support minimally invasive access port-based surgery.

Referring to FIG. 2, an exemplary navigation system environment 200 is shown, which may be used to support navigated image-guided surgery. As shown in FIG. 2, surgeon 201 conducts a surgery on a patient 202 in an operating room (OR) environment. A medical navigation system 205 comprising an equipment tower, tracking system, displays and tracked instruments assist the surgeon 201 during his procedure. An operator 203 is also present to operate, control and provide assistance for the medical navigation system 205.

Figure 3:
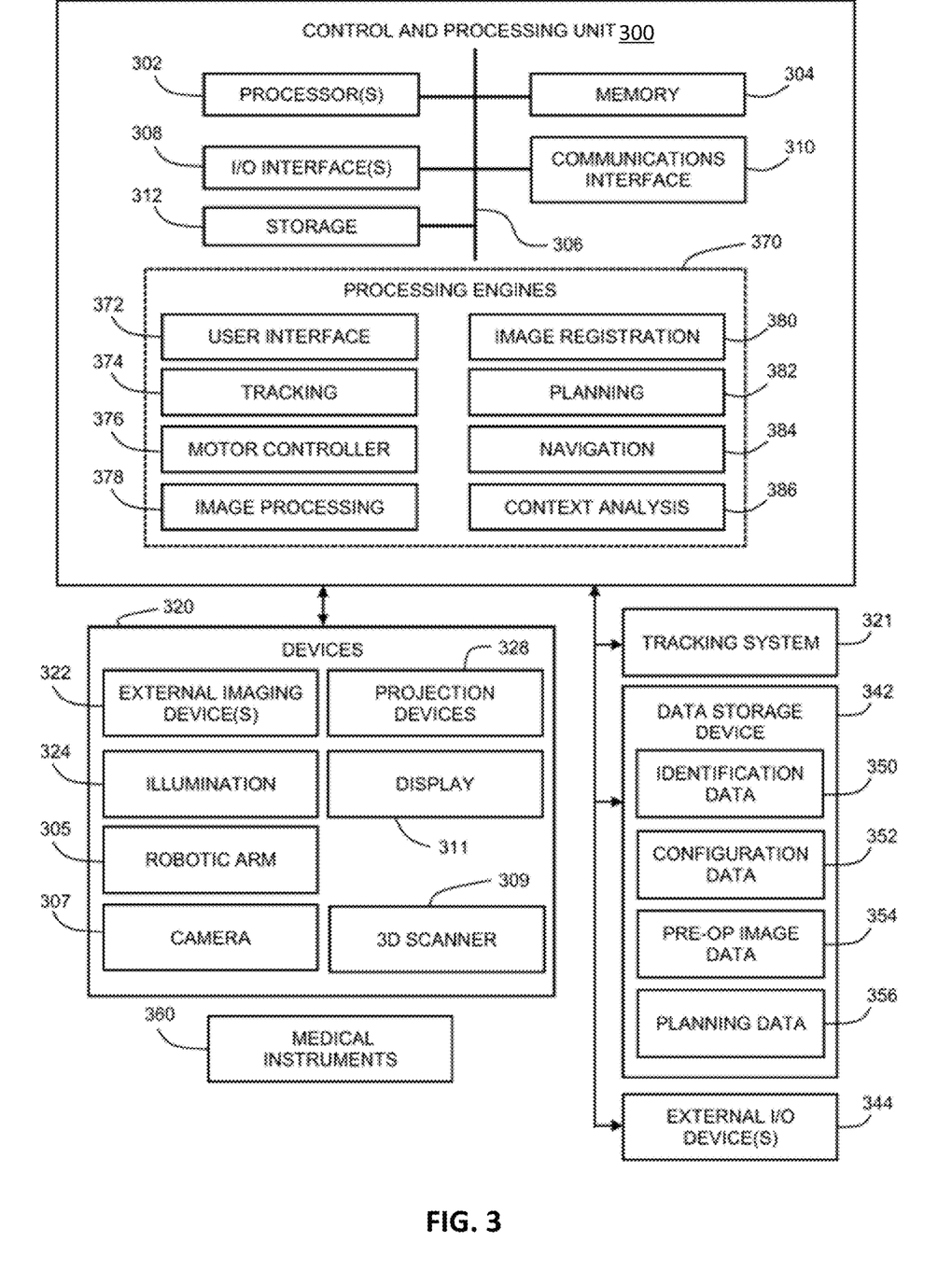
FIG. 3 is a block diagram illustrating a control and processing system that may be used in the navigation system shown in FIG. 2.

Referring to FIG. 3, a block diagram is shown illustrating a control and processing system 300 that may be used in the medical navigation system 200 shown in FIG. 2 (e.g., as part of the equipment tower). As shown in FIG. 3, in one example, control and processing system 300 may include one or more processors 302, a memory 304, a system bus 306, one or more input/output interfaces 308, a communications interface 310, and storage device 312. Control and processing system 300 may be interfaced with other external devices, such as tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage 342 includes identification data 350 for identifying one or more medical instruments 360 and configuration data 352 that associates customized configuration parameters with one or more medical instruments 360. Data storage 342 may also include preoperative image data 354 and/or medical procedure planning data 356. Although data storage 342 is shown as a single device in FIG. 3, it will be understood that in other embodiments, data storage 342 may be provided as multiple storage devices.

Medical instruments 360 are identifiable by control and processing system 300. Medical instruments 360 may be connected to and controlled by control and processing system 300, or medical instruments 360 may be operated or otherwise employed independent of control and processing system 300. Tracking system 321 may be employed to track one or more of medical instruments 360 and spatially register the one or more tracked medical instruments to an intraoperative reference frame. For example, medical instruments 360 may include tracking markers such as tracking spheres that may be recognizable by a tracking camera 307. In one example, the tracking camera 307 may be an infrared (IR) tracking camera. In another example, as sheath placed over a medical instrument 360 may be connected to and controlled by control and processing system 300.

Control and processing system 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, a robotic arm 305, one or more projection devices 328, a 3D scanner 309, and one or more displays 311. It should be noted that the 3D scanner may include devices such as a preoperative or intraoperative CT, MRI, Ultrasound, OCT, or Structured light imaging probes and the like.

Exemplary aspects of the disclosure may be implemented via processor(s) 302 and/or memory 304. For example, the functionalities described herein can be partially implemented via hardware logic in processor 302 and partially using the instructions stored in memory 304, as one or more processing modules 370 (or engines). Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example the processing modules 370 may be stored in the memory 304 and the processing modules may be collectively referred to as processing modules 370.

It is to be understood that the system is not intended to be limited to the components shown in FIG. 3. One or more components of the control and processing system 300 may be provided as an external component or device. In one example, navigation engine 384 may be provided as an external navigation system that is integrated with control and processing system 300.

Some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

According to one aspect of the present application, one purpose of the navigation system 205, which may include control and processing unit 300, is to provide tools to the neurosurgeon that will lead to the most informed, least damaging neurosurgical operations. In addition to removal of brain tumors and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

While one example of a navigation system 205 is provided that may be used with aspects of the present application, any suitable navigation system may be used, such as a navigation system using optical tracking instead of infrared cameras.

Figure 4A:
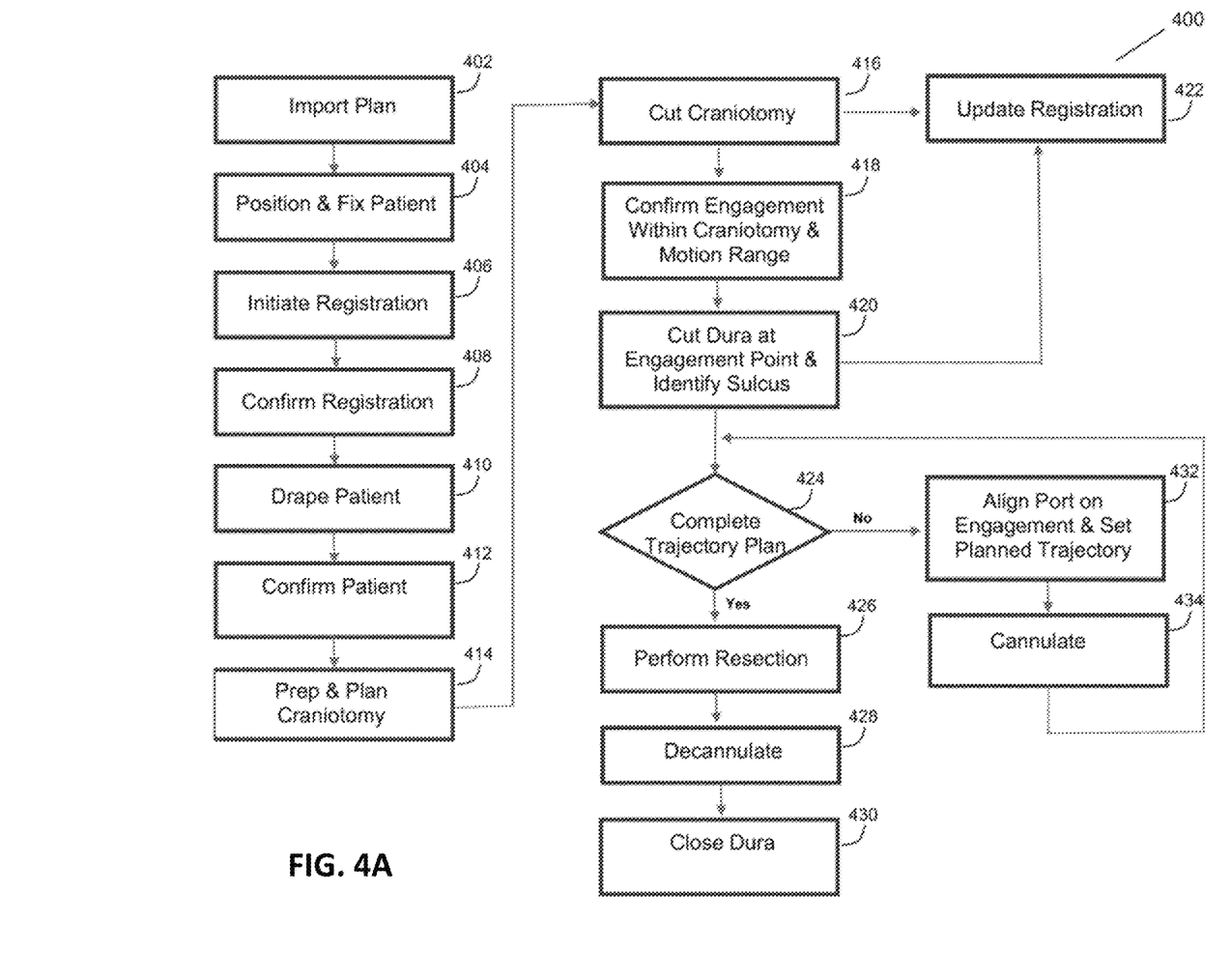
FIG. 4A is a flow chart illustrating a method involved in a surgical procedure using the navigation system of FIG. 2.

Referring to FIG. 4A, a flow chart is shown illustrating a method 400 of performing a port-based surgical procedure using a navigation system, such as the medical navigation system 205 described in relation to FIG. 2. At a first block 402, the port-based surgical plan is imported. A detailed description of the process to create and select a surgical plan is outlined in international publication WO/2014/139024, entitled "PLANNING, NAVIGATION AND SIMULATION SYSTEMS AND METHODS FOR MINIMALLY INVASIVE THERAPY", which claims priority to U.S. Provisional Patent Application Ser. Nos. 61/800,155 and 61/924,993, which are all hereby incorporated by reference in their entirety.

Once the plan has been imported into the navigation system at the block 402, the patient is placed on a surgical bed. The head position is confirmed with the patient plan in the navigation system (block 404), which in one example may be implemented by a computer or controller forming part of the equipment tower.

Next, registration of the patient is initiated (block 406). The phrase "registration" or "image registration" refers to the process of transforming different sets of data into one coordinate system. Data may include multiple photographs, data from different sensors, times, depths, or viewpoints. The process of "registration" may be used for medical imaging in which images from different imaging modalities are co-registered. In some instances registration may also be used in order to be able to compare, map, or integrate the data obtained from these different modalities with a position of a patient in physical space.

Those skilled in the relevant arts will appreciate that there are numerous registration techniques available and one or more of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in MRI and PET. In the present disclosure, multi-modality registration methods may be used in medical imaging of the head and/or brain as images of a subject are frequently obtained from different scanners. Examples include registration of brain CT/MRI images or PET/CT images for tumor localization, registration of contrast-enhanced CT images against non-contrast-enhanced CT images, and registration of ultrasound and CT to patient in physical space.

Figure 4B:
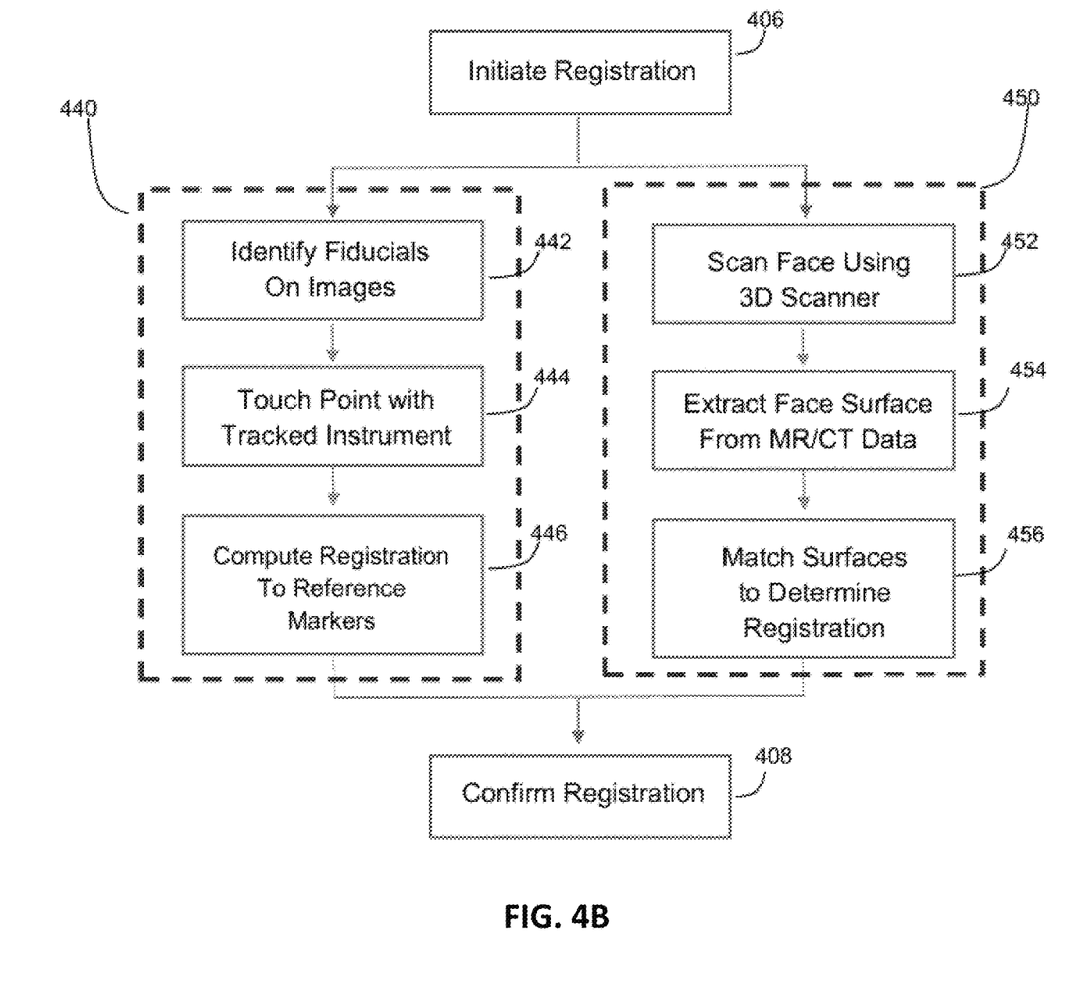
FIG. 4B is a flow chart illustrating a method of registering a patient for a surgical procedure as outlined in FIG. 4A.

Referring now to FIG. 4B, a flow chart is shown illustrating two methods which may occur as per registration block 406, outlined in FIG. 4A, in greater detail. If the use of fiducial touch points (440) is contemplated, the method involves first identifying fiducials on images (block 442), then touching the touch points with a tracked instrument (block 444). Next, the navigation system computes the patient registration to reference markers (block 446).

Alternately, registration can also be completed by conducting a surface scan procedure (block 450), which may be applied to aspects of the present disclosure. The block 450 is presented to show an alternative approach. First, the face is scanned using a 3D scanner (block 452). Next, the face surface is extracted from MR/CT data (block 454). Finally, surfaces are matched to determine registration data points (block 456).

Upon completion of either the fiducial touch points (440) or surface scan (450) procedures, the data extracted is computed and used to confirm registration at block 408, shown in FIG. 4A.

Referring back to FIG. 4A, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms (e.g., bacteria) between non-sterile and sterile areas. At this point, conventional navigation systems require that the non-sterile patient reference is replaced with a sterile patient reference of identical geometry location and orientation. Numerous mechanical methods may be used to minimize the displacement of the new sterile patient reference relative to the non-sterile one that was used for registration but it is inevitable that some error will exist. This error directly translates into registration error between the surgical field and pre-surgical images. In fact, generally the further away points of interest are from the patient reference, the worse the error will be.

Upon completion of draping (block 410), the patient engagement points are confirmed (block 412) and then the craniotomy is prepared and planned (block 414).

Upon completion of the preparation and planning of the craniotomy (block 414), the craniotomy is cut and a bone flap is temporarily removed from the skull to access the brain (block 416). Registration data is updated with the navigation system at this point (block 422).

Next, the engagement within craniotomy and the motion range are confirmed (block 418). Next, the procedure advances to cutting the dura at the engagement points and identifying the sulcus (block 420).

Thereafter, the trajectory plan is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIG. 4A are specific to port-based surgery, such as portions of blocks 428, 432, and 434, but the appropriate portions of these blocks may be skipped or suitably modified when performing non-port based surgery.

Figure 5:
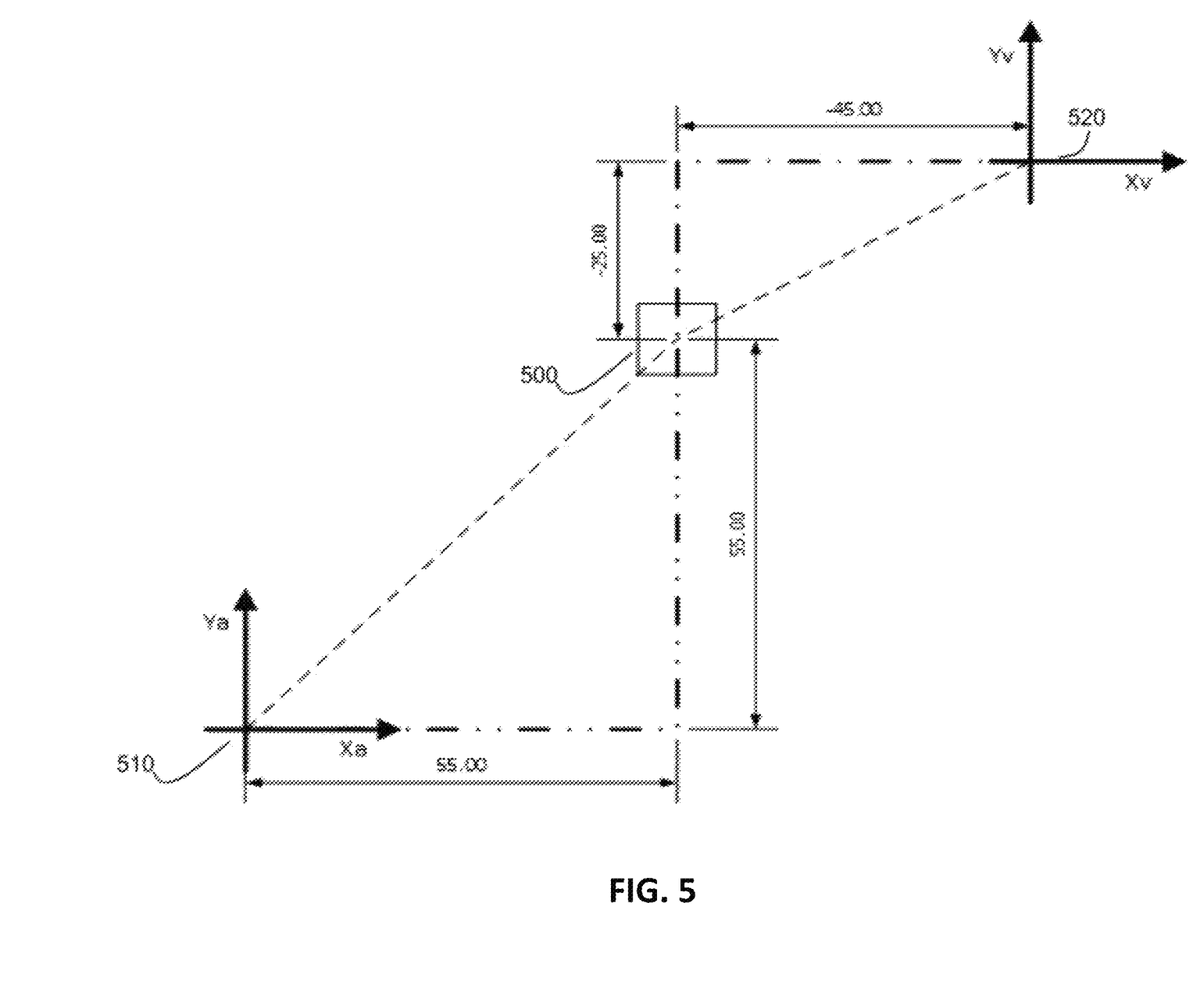
FIG. 5 illustrates an explanatory diagram regarding the coupling of two coordinate spaces.

Referring now to FIG. 5, a registration process, similar to that which may be used in block 456 of FIG. 4B, is shown for computing a transform that may be used to import coordinates from the physical coordinate space of the operating room to the image space of the MRI image. Resultantly any tool positions in the physical coordinate space may be registered to the image space via the application of this transform.

In order to derive this transform for importing objects from a physical coordinate space to an image space, the two spaces must be coupled with a "common reference", having a defined position that can be located in both the physical and image coordinate spaces. The process of patient registration for surgical navigation uses identifiable points located on a patient anatomy visible both on the patient and on the patients scan as the common reference point(s). An example of a common reference is shown in FIG. 5 as 500 along with the physical and image coordinate space origins, 510 and 520 respectively. It is apparent from the figure that the common references position is known in both spaces. Using these positions a transform may be derived that facilitates the importation of the position of any point in the physical coordinate space into the image space. One way to determine the transform is by equating the locations of the common reference in both spaces and solving for an unknown translation variable for each degree of freedom defined in the two coordinate spaces. These translation variables may then be used to convert a set of coordinates from one space to the other. An exemplary transform may be derived as per the diagram shown in FIG. 5. In the figure the position of the common reference 500 is known relative to the physical coordinate space origin 510 and the image space origin 520. The common references position can be extracted from the diagram as follows:

$$(X_{cra}, Y_{cra}) = (55, 55)$$

and $$(X_{crv}, Y_{crv}) = (-45, -25)$$

Where the subscript "cra" denotes the common reference position relative to the physical coordinate space origin and the subscript "crv" denotes the common reference position relative to the image space origin. Utilizing a generic translation equation describing any points $((Y_a, X_a)$ and $(Y_v, X_v))$, where the subscript "a" denotes the coordinates of a point relative to the physical coordinate space origin 510, and the subscript "v" denotes the coordinates of a point relative to the image space origin 520, we can equate the individual coordinate elements from each space to solve for translation variables $((Y_T, X_T))$, where the subscript "T" denotes the translation variable as shown below.

$$Y_v = Y_a + Y_T$$

$$X_v = X_a + X_T$$

Now substituting the derived values of the points from FIG. 5 we can solve for the translation variable.

$$-25 = 55 + Y_T$$

$$-80 = Y_T$$

and $$-45 = 55 + X_T$$

$$-100 = X_T$$

Utilizing these translation variables, any position ((i.e. $(Y_a, X_a)$)) defined relative to the common reference in the physical coordinate space may be transformed into an equivalent position defined relative to the common reference in the image space through the two generic transformation equations provided below. It should be noted that these equations may be rearranged to transform any coordinates of a position from the image space into equivalent coordinates of a position in the physical coordinate space as well.

$$X_a = X_v + 100$$

and $$Y_a = Y_v + 80$$

The calculated transform thus enables the position of any object to be transformed from the physical coordinate space to the image space. Thus the two spaces become coupled with the transform enabling the registration of objects from the physical space to the image space. It should be noted that in practice the common reference is usually a set of points (as opposed to a single point) from the patients anatomy that may be located both on the anatomy of the patient in the physical coordinate space of the operating room and in the image of the patient. Using a set of points may be more advantages as it further restricts degrees of freedom. More specifically in a spatial coordinate system such as the physical coordinate space of the operating room an object may have six degrees of freedom, three spatial degrees of freedom most commonly referred to as (x, y, z) and three rotational degrees most commonly referred to as (pitch, yaw, roll). Accordingly one manner to duplicate these values upon transformation from the physical coordinate space to the image space is to transform three or more points from the object.

Figure 6:
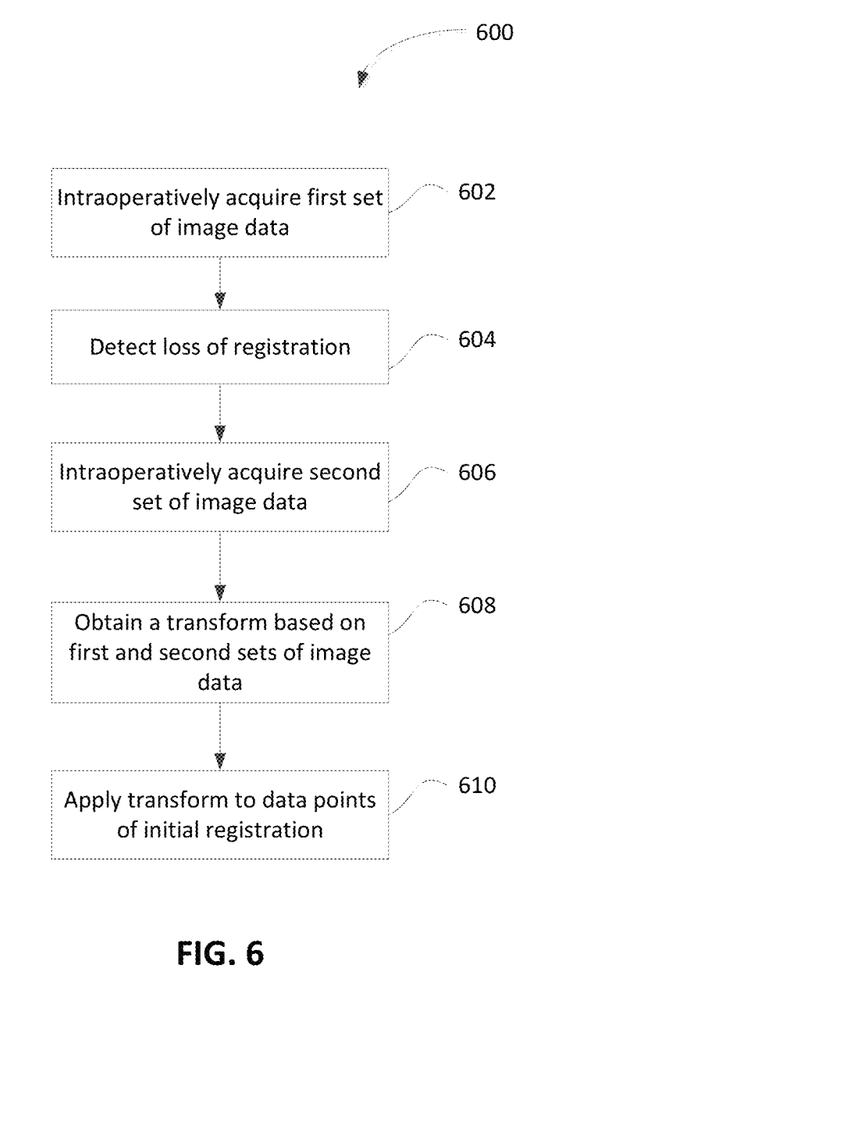
FIG. 6 is a flow chart illustrating an example method of updating a patient registration for a surgical procedure with a medical navigation system.

Reference is now made to FIG. 6, which shows an example method 600 for recovering from a loss of patient registration. The method 600 may be implemented by a control system for a surgical navigation system, such as the control and processing system 300 of FIG. 3. The method 600 may be used to update or correct a patient registration in a surgical procedure which involves the creation of anatomical landmarks on the patient's body as a part of the surgical workflow. For example, the method 600 may be suitable for use in obtaining an updated registration in a craniotomy procedure, which involves the temporary removal of a bone flap from the patient's skull to access the brain.

In operation 602, a first set of image data depicting a region of interest on the patient is acquired intraoperatively, where the region of interest includes at least one anatomical landmark created as part of the surgical procedure. For example, the region of interest may include a surgical opening created during a craniotomy procedure. In at least some embodiments, the first set of image data includes at least magnetic resonance (MR) image data (e.g. MR coordinates taken from an MR scan) of the region of interest, and three-dimensional (3D) scan data depicting the region of interest and the patient reference object. In particular, the patient reference is visible to a 3D scanner of the surgical navigation system that is used to generate 3D scan data that is representative of a 3D scan of at least part of the patient anatomy.

In at least some embodiments, the first set of image data can be registered in association with the at least one anatomical landmark. For example, intraoperatively acquired MR image and 3D scan data depicting a surgical opening of a craniotomy may be stored and registered to the patient space and/or the navigation space. It should be noted that, while the initial patient registration is intact, the registration of an anatomical landmark, such as a craniotomy opening, can be mapped to the initial patient registration. For example, in a craniotomy procedure, as the precise location of the craniotomy opening relative to the patient's skull will be known (e.g. from the MR image and 3D scan), the craniotomy registration can be related to the initial patient registration by point wise matching of coordinate data points.

In operation 604, a loss of the patient registration or a registration error is detected. The loss of registration may be detected directly by the surgeon if movement of a part of a patient's body (e.g. patient's head) and/or the patient reference is noticed. For example, a loss of registration may be detected when the surgeon detects movement of the patient's head (i.e. displacement of the head from a fixed initial position) during the surgical operation (and similarly, movement of the patient reference with respect to its initial position). Such movement of the patient's body and/or patient reference object may be detected via visual inspection, with or without the assistance of a tracking camera. Upon noting a displacement of the patient's body or patient reference, the surgeon may input, using an input device, to a controller of the surgical navigation system, an indication that a potential loss of registration has been detected. In some embodiments, the surgical navigation system may include a detection unit that is configured to monitor the positions of the patient and patient reference, respectively. Such detection unit may be set up to generate a message or an alert upon detecting a displacement (e.g. displacement by an amount that is greater than a predefined threshold), of either the patient's body or the patient reference. The alert/message may then be transmitted to the surgical navigation system, flagging a potential loss of patient registration.

In some embodiments, a presence of misalignment in virtual and real objects during image-guided surgery may indicate a loss of (or incorrect) registration. For example, when virtual images containing one or more virtual objects (e.g. surgical tools) that have been previously registered as part of the surgical navigation system are overlaid onto intraoperatively acquired images of the surgical field containing the real objects corresponding to the one or more virtual objects, a misalignment or non-concordance may be detected. Such misalignment may, in turn, be readily noticeable and indicative of a registration error between a virtual object and its corresponding real object.

In operation 606, after the registration error or loss is detected and communicated to the controller for the surgical navigation system, a second set of image data depicting the region of interest is acquired. In at least some embodiments, the second set of image data includes at least magnetic resonance (MR) image data of the region of interest, and three-dimensional (3D) scan data depicting the region of interest and the patient reference object. The second set of image data may be acquired in response to a manual request from an individual (e.g. a surgeon) that detects a potential loss of registration. For example, if a user-input indicating that the patient registration may be lost is received at the navigation system, a second set of image data including the region of interest may be caused to be acquired.

In operation 608, a transform based on the first set of image data and the second set of image data is identified. In particular, where a registration loss occurs as a result of bumping part of a patient's body (e.g. patient's head) or the patient reference, the identified transform will be based on the relative displacement of the patient's body part with respect to the patient reference. The step of identifying the relevant transform will be detailed below with respect to FIGS. 7 and 8.

In operation 610, the identified transform is applied to data points of the patient registration to obtain data points for an updated registration. As noted above, the registration of the anatomical landmark (e.g. a craniotomy opening) depicted in the first set of image data can be mapped to the initial pre-loss patient registration. The transform identified in operation 608, which is based on the relative displacement between the patient's body and the patient reference as noted from the first and second sets of image data, can be applied to the data points of the initial patient registration such that said relative displacement is reflected in the data points of the updated/corrected registration.

Figure 7:
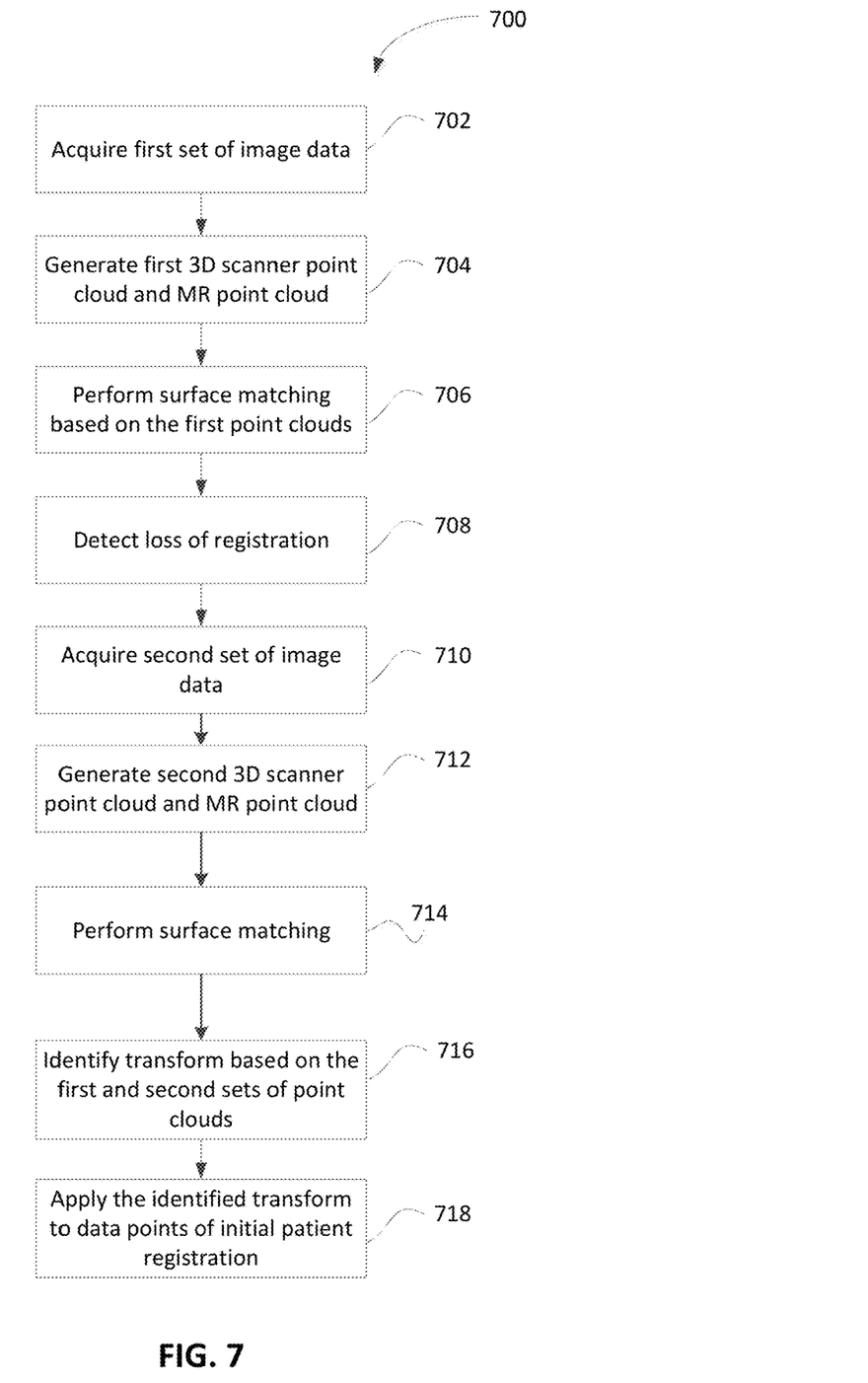
FIG. 7 is a flow chart illustrating another example method for updating a patient registration for a surgical procedure with a medical navigation system.

Reference is now made to FIG. 7, which shows, in flowchart form, an example method 700 for recovering a lost registration. The method 700 may be implemented by a control system for a surgical navigation system, such as the control and processing system 300 of FIG. 3. The method 700 may be used to update or correct a patient registration in a surgical procedure (e.g. craniotomy) which involves the creation of one or more anatomical landmarks on the patient's body as a part of the surgical workflow.

In operation 702, a first set of image data depicting a region that includes an anatomical landmark of interest is acquired intraoperatively. The first set of image data includes at least one MR volumetric scan data (image) of the region of interest and at least one 3D scan depicting the patient reference and the region of interest. In operation 704, a 3D scanner point cloud is generated from the 3D scan data and one or more surfaces are extracted from the MR image data to generate an MR point cloud. In operation 706, a surface matching is performed based on the 3D scanner point cloud and the MR point cloud. Provided that the anatomical landmark (e.g. craniotomy opening) includes unique and/or distinguishable features (i.e. size, shape, thickness of the bone, location of opening, etc.), the surfaces may be matched to a high degree of accuracy. Other features, including size, shape and location of brain folds, dura, and/or masses of blood vessels (arteries and veins) may be used to assist in surface matching. This surface matching can then form the basis for registering the anatomical landmark (or anatomical region of interest). This registration may include, for example, registering the MR extracted surface (s) to the 3D scanner point cloud.

In operation 708, a loss of registration is detected and reported/broadcast. In response to the detection of registration loss, or in response to receiving an express instruction to recover a registration, a second set of image data is acquired in operation 710. The second set of image data includes at least one MR volumetric scan data (image) of the region of interest and at least one 3D scan depicting the patient reference and the region of interest. In operation 712, point cloud data is generated from the second MR and 3D scans, and in operation 714, surface matching is performed based on said point cloud data. The aligned surfaces from the 3D scanner point cloud and the MR point cloud may then be registered.

In operation 716, a transform reflecting the relative displacement of the patient's body with respect to the patient reference is identified, based on the first and second sets of image data. In at least some embodiments, the transform is identified based on registrations of the MR and 3D scanner point clouds corresponding to the first image set and the second image set, respectively. That is, if, as a result of registering the point clouds, the aligned surfaces are integrated to a single reference frame (e.g. 3D scanner space or imaging space), the change in relative positions of the patient's body and the patient reference can be determined. This change in relative positions can then form the basis of the transform from the initial patient registration to an updated/corrected registration. Finally, in operation 718, the transform identified in operation 716 is applied to the initial patient registration.

Figure 8:
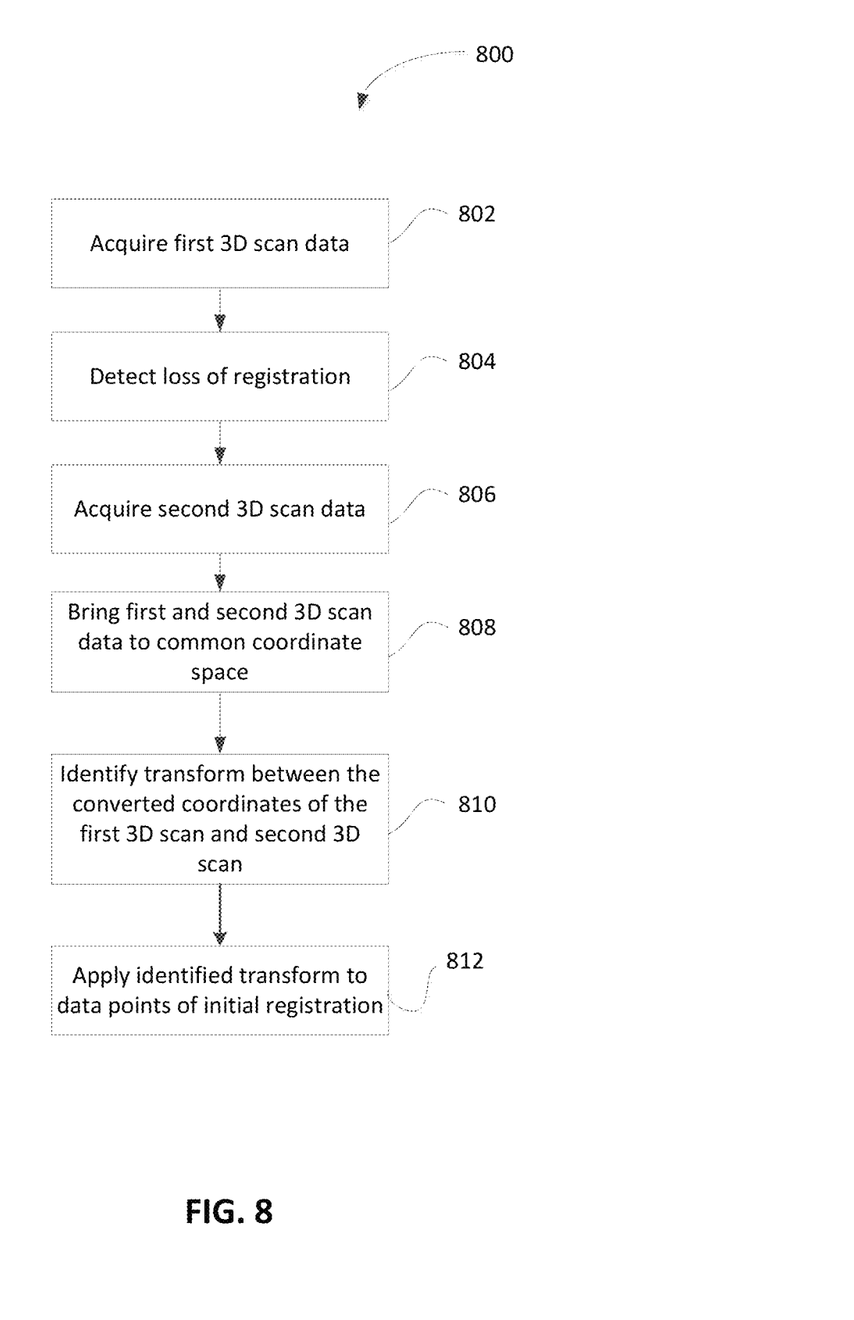
FIG. 8 is a flow chart illustrating another example method for updating a patient registration for a surgical procedure with a medical navigation system.

Reference is now made to FIG. 8, which shows, in flowchart form, another method 800 for recovering from a loss of registration. The method 800 may be used to update a patient registration after detecting a loss of a previous (or initial) registration during a surgical procedure. The surgical procedure includes a navigation system having a tracking system for optically tracking a patient reference object and a 3D scanner for generating 3D scan data of the surgical field.

In operation 802, first 3D scan data depicting a region that includes an anatomical landmark of interest, such as a craniotomy opening, are acquired intraoperatively. In response to detecting a loss of registration (or registration error) in operation 804, second 3D scan data are acquired in operation 806.

The 3D scan data can be visualized in a common coordinate space based on the 3D scanner's calibration. More specifically, a transformation, $T_{prs}$, which brings both the first 3D scan data and the second 3D scan data to a common coordinate space, may be determined. In at least some embodiments, obtaining the transformation $T_{prs}$ may comprise deriving a first transformation, $T_1$, which maps the 3D scan data to the tracking system's camera space, and a second transformation, $T_2$, which represents a transform from patient reference to camera space, obtained by tracking the patient reference in camera space. In particular, $$T_{prs} = T_2^{-1} \times T_1$$

brings data points from the 3D scans to the coordinate space of the patient reference, where $T_2^{-1}$ is the reverse transform to patient reference space.

In operation 808, the transformation $T_{prs}$ is applied to the first 3D scan data and the second 3D scan data. The transformed coordinates of the first 3D scan data are then registered to the transformed coordinates of the second 3D scan data. In this way, the spatial transform (e.g. translation, etc.) of the patient's body with respect to the patient reference can be determined. This spatial transform, obtained in operation 810, can subsequently be applied to data points of the initial patient registration to obtain data points for an updated/corrected patient registration (operation 812).

In some embodiments, the methods 600, 700, and/or 800 may employ an Iterative Closest Point (ICP) approach to calculate the respective registration transformations, such as that detailed in "A Method for Registration of 3-D Shapes" by Paul J. Besl and Neil D. McKay, IEEE Transactions on Pattern Analysis and Machine Intelligence, pp. 239-256, vol. 14, no. 2, February 1992, the entirety of which is hereby incorporated by reference. However, any suitable approach may be used depending on the design criteria of a particular application.

The specific embodiments described above have been shown by way of example, and it should be understood that these embodiments may be susceptible to various modifications and alternative forms. It should be further understood that the claims are not intended to be limited to the particular forms disclosed, but rather to cover modifications, equivalents, and alternatives falling within the spirit and scope of this disclosure.

Some aspects of the present disclosure can be embodied, at least in part, in software, which, when executed on a computing system, transforms an otherwise generic computing system into a specialty-purpose computing system that is capable of performing the methods disclosed herein, or variations thereof. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSIs), application-specific integrated circuits (ASICs), or firmware such as electrically erasable programmable read-only memory (EEPROMs) and field-programmable gate arrays (FPGAs).

A computer readable storage medium can be used to store software and data which when executed by a data processing system causes the system to perform various methods. The executable software and data may be stored in various places including for example ROM, volatile RAM, non-volatile memory and/or cache. Portions of this software and/or data may be stored in any one of these storage devices. As used herein, the phrases "computer readable material" and "computer readable storage medium" refers to all computer-readable media, except for a transitory propagating signal per se.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The various embodiments presented above are merely examples and are in no way meant to limit the scope of this application. Variations of the innovations described herein will be apparent to persons of ordinary skill in the art, such variations being within the intended scope of the present application. In particular, features from one or more of the above-described example embodiments may be selected to create alternative example embodiments including a sub-combination of features which may not be explicitly described above. In addition, features from one or more of the above-described example embodiments may be selected and combined to create alternative example embodiments including a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A computer-implemented method for updating a first patient registration during a surgical procedure that uses an optical navigation system for optically tracking a patient reference object in a real world space, the surgical procedure including intra-operatively acquiring a first set of image data depicting a region of interest on the patient while the first registration is intact, the region of interest including at least one anatomical landmark, the method comprising:
   detecting that the first registration has been lost;
   obtaining a second set of image data depicting the region of interest;
   identifying a transform based on the first set of image data and the second set of image data; and
   applying the identified transform to data points of the first registration to obtain data points for the updated patient registration.

2. The method of claim 1, wherein the first set of image data and the second set of image data both include:
   magnetic resonance (MR) image data of the region of interest; and
   three-dimensional (3D) scan data depicting the patient reference object and the region of interest.

3. The method of claim 2, wherein identifying the transform comprises:
   performing a surface extraction from the MR image data to generate an MR point cloud;
   generating a 3D scanner point cloud of the region of interest and the patient reference object based on the 3D scan data; and
   performing surface matching based on the MR point cloud and the 3D scanner point cloud.

4. The method of claim 3, further comprising registering the MR point cloud to the 3D scanner point cloud.

5. The method of claim 1, wherein the at least one anatomical landmark comprises a surgically created opening on the patient's body.

6. The method of claim 5, wherein the at least one anatomical landmark comprises a surgical opening on the patient's skull.

7. The method of claim 1, wherein detecting that the first registration has been lost comprises detecting movement of the patient's head relative to the patient reference object during the surgical procedure.

8. The method of claim 1, wherein detecting that the first registration has been lost comprises detecting movement of the patient reference object with respect to the patient's body.

9. The method of claim 1, wherein detecting that the first registration has been lost comprises detecting a registration error between one or more previously registered virtual objects and corresponding real objects in intra-operatively acquired images.

10. The method of claim 1, further comprising receiving a user inputted indication that the first registration has been lost, wherein the obtaining the second set of image data is performed in response to receiving the user inputted indication.

11. A computer-implemented method for updating a first patient registration during a surgical procedure that uses an optical navigation system including a tracking system for optically tracking a patient reference object in a real world space and a 3D scanner for generating 3D scan data, the surgical procedure including intra-operatively acquiring first 3D scan data while the first registration is intact, the first 3D scan data depicting the patient reference object and a region of interest on the patient that includes at least one anatomical landmark, the method comprising:
   detecting that the first registration has been lost;
   obtaining second 3D scan data depicting the patient reference object and the region of interest;
   identifying a transform based on the 3D scan data and the second 3D scan data; and
   applying the identified transform to data points of the first registration to obtain data points for the updated patient registration.

12. The method of claim 11, wherein the at least one anatomical landmark comprises a surgically created opening on the patient's body.

13. The method of claim 12, wherein the at least one anatomical landmark comprises a surgical opening on the patient's skull.

14. The method of claim 11, wherein detecting that the first registration has been lost comprises detecting movement of the patient's head relative to the patient reference object during the surgical operation.

15. The method of claim 11, wherein detecting that the first registration has been lost comprises detecting movement of the patient reference object with respect to the patient's body.

16. The method of claim 11, wherein detecting that the first registration has been lost comprises detecting a registration error between one or more previously registered virtual objects and corresponding real objects in intra-operatively acquired images.

17. The method of claim 11, wherein identifying the transform comprises determining a transform between a camera space of the tracking system and a coordinate space of the 3D scanner.

18. The method of claim 11, wherein identifying the transform comprises registering the first 3D scan data to the second 3D scan data.

* * * * *